US006972180B1

(12) United States Patent
Streckfus et al.

(10) Patent No.: US 6,972,180 B1
(45) Date of Patent: Dec. 6, 2005

(54) METHOD OF DIAGNOSING AND MONITORING MALIGNANT BREAST CARCINOMAS

(75) Inventors: Charles F. Streckfus, Brandon, MS (US); Lenora G. Bigler, Clinton, MS (US); James Tate Thigpen, Jackson, MS (US)

(73) Assignee: The University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 09/914,501

(22) PCT Filed: Mar. 1, 2000

(86) PCT No.: PCT/US00/05364

§ 371 (c)(1),
(2), (4) Date: Dec. 13, 2001

(87) PCT Pub. No.: WO00/52463

PCT Pub. Date: Sep. 8, 2000

Related U.S. Application Data

(63) Continuation-in-part of application No. 09/259,993, filed on Mar. 1, 1999, now Pat. No. 6,294,349.

(51) Int. Cl.[7] ..................... G01N 33/574; G01N 33/53; G01N 33/68

(52) U.S. Cl. ................... 435/7.23; 435/4; 435/7.1; 435/7.2; 435/7.21; 435/7.92; 435/7.93; 435/7.94; 436/501; 436/63; 436/64

(58) Field of Search ................... 435/7.1, 7.21, 435/7.23, 6, 4, 7.92, 7.93, 7.94, 7.95; 436/501, 436/503, 69, 63, 64

(56) References Cited

U.S. PATENT DOCUMENTS

| | | |
|---|---|---|
| 5,401,638 A | 3/1995 | Carney et al. |
| 5,512,657 A | 4/1996 | Van Aken et al. |
| 5,527,676 A | 6/1996 | Vogelstein et al. |
| 5,769,074 A | 6/1998 | Barnhill et al. |
| 5,840,889 A | 11/1998 | Cavalieri et al. |
| 5,858,365 A | 1/1999 | Faller |
| 5,858,683 A | 1/1999 | Keesee et al. |
| 6,294,349 B1 * | 9/2001 | Streckfus et al. .......... 435/7.23 |

FOREIGN PATENT DOCUMENTS

| | | |
|---|---|---|
| WO | WO 91/02062 | 2/1991 |
| WO | WO 00/44403 | 8/2000 |

OTHER PUBLICATIONS

Streckfus et al., The presencre of CA 15-3, c-erbB-2, cathepsin-D, EGFR, WAF1, and p53 in saliva among women with benign and malignant breast disease., The Journal of Dental Research, vol. 77, pp. 286, Abstract# 1437, Jan. 1998.*
Streckfus, et al. "The Presence of CA 15-3, c-erB-2, Cathespin-D, EGFR, WAF1 and p53 in Saliva Among Women with Benign and Malignant Tumors." *Journal of Dental Research*, Jan. 30, 1998, p. 285, #1437, vol. 77. University of Mississippi Medical Center, Jackson, MS.
Dobrosielski-Vergona, K., Biology of University of Pittsburgh, Pittsburgh, Pennsylvania, PA, CRC Press, Inc., Boca Raton, FL.
Baum, B., "Age Changes in Salivary Glands and Salivary Secretion," Chapter 8: *Geriatric Dentistry —A Textbook of Oral Gerontology;* Edited by: Holm-Pedersen, P., and Loe, H., The C.V. Mosby Company, St. Louis; Washington, DC; Toronto.
Cook, D.I., et al., "Secretion by the Major Salivary Glandsp", Chapter 26: *Physiology of the Gastrointestinal Tract*, 1994, pp. 1061-1117, Third Edition, Raven Press, New York.
Sreebny, L., "The Salivary System", *Dept. of Oral Biology and Pathology*, pp. 128-131, State University of New York at Stony Brook, Stony Brok, New York, CRC Press, Inc., Boca Raton, Florida.
Chen, D., "Saliva and Serum CA 125 Assays for Detecting Malignant Ovarian Tumors", *Dept. of Obstetrics and Gynecology*, First Affiliated Hospital, Human Medical University, People's Republic of China, and the *Dept. of Obstetrics and Gynecology*, Yale University, School of Medicine, New Haven, Connecticut, Apr. 1990,. pp. 701-703, vol. 75, No. 4.
Mandel, I., "Sialochemistry in Diseases and Clinical Situations Affecting Salivary Glands", *CRC Critical Reviews in Clinical Laboratory Sciences*, Sep. 1980, pp. 321-366, New York, New York.

* cited by examiner

*Primary Examiner*—Jeffrey Siew
*Assistant Examiner*—Anne L. Holleran
(74) *Attorney, Agent, or Firm*—Stites & Harbison PLLC; Richard S. Myers, Jr.

(57) ABSTRACT

A panel of biomarkers for the diagnosis and treatment of breast cancer was examined in the saliva of a cohort of 1) healthy women, 2) women with benign lesions of the breast and 3) women with diagnosed breast cancer. Recognized tumor markers c-erbB-2 (erb), cancer antigen 15-3 (CA 15-3), and tumor suppresser oncogene protein 53 (p53) were found in the saliva of all three groups of women. The levels of erb and CA 15-3 in the cancer patients evaluated, however, were significantly higher than the salivary levels of healthy controls and benign tumor patients. Conversely, pantropic p53 levels were higher in controls as compared to those women with breast cancer and those with benign tumors.

13 Claims, 15 Drawing Sheets

| MEDIUM | STATUS | CA 15-3 U/mg OF PROTEIN | erb UNITS/mg OF PROTEIN | p53 PMOL/mg OF PROTEIN | CD PMOL/mg OF PROTEIN | EGFR FMOL/mg OF PROTEIN | TOTAL PROTEIN mg/ml |
|---|---|---|---|---|---|---|---|
| SALIVA | CONTROLS (n=15) | 2.27 ± 1.45 | NOT DETECTABLE | 177.1 ± 61.3 | 26.29 ± 17.22 | 1.03 ± 0.69 | 1.25 ± 0.82 |
| SALIVA | BENIGN (n=8) | 2.22 ± 1.95 | NOT DETECTABLE | 180.7 ± 70.78 | 40.57 ± 13.05 | 0.37 ± 0.31 | 1.44 ± 0.92 |
| SALIVA | Ca IN SITU (n=12) | 5.26 ± 4.12* | 51.3 ± 43.96± | 134.6 ± 63.8 | 34.5 ± 27.95 | 0.92 ± 0.8 | 1.71 ± 0.79 |
| SERUM | CONTROLS (n=15) | 16.17 ± 4.64 | NOT DETECTABLE | 14.2 ± 7.9 | 67.5 ± 35.61 | 8.5 ± 8.45 | 24.54 ± 13.86 |
| SERUM | BENIGN (n=8) | 15.25 ± 5.04 | NOT DETECTABLE | 14.63 ± 8.8 | 45.0 ± 20.98 | 3.52 ± 1.89 | 27.33 ± 14.23 |
| SERUM | Ca IN SITU (n=12) | 24.68 ± 10.9** | 81.68 ± 111.77# | 8.9 ± 7.7 | 63.17 ± 38.4 | 5.63 ± 3.10 | 29.23 ± 11.08 |

FIG. 1

MEAN AND STANDARD ERROR OF THE MEAN (S.E.M.) VALUES FOR c-erbB-2

| CHARACTERISTICS | HEALTHY CONTROLS | | | BENIGN TUMORS | | | MALIGNANT TUMORS | | |
|---|---|---|---|---|---|---|---|---|---|
| | n | AGE | MEAN (S.E.M.) | n | AGE | MEAN (S.E.M.) | n | AGE | MEAN (S.E.M.) |
| SALIVA c-erbB-2 | 57 | 39.6 | 94.70 (±8.39) | 41 | 45.0 | 99.72 (±10.94) | 30 | 50.8 | 222.22 (±19.22) |
| SALIVA c-erbB-2 (UNITS/mg PROTEIN) | 57 | 39.6 | 71.13 (±6.07) | 41 | 45.0 | 63.75 (±7.00) | 30 | 50.8 | 143.58 (±11.53) |
| SALIVARY PROTEIN (mg/ml) | 56 | 39.3 | 1.48 (±0.09) | 41 | 45.0 | 1.58 (±0.08) | 30 | 50.8 | 1.67 (±0.10) |
| SALIVARY CA 15-3 (UNITS/ml) | 42 | 38.0 | 3.19 (±0.52) | 33 | 43.9 | 7.23 (±1.58) | 30 | 50.8 | 10.90 (±3.44) |
| SALIVARY FLOW RATES (ml/min.) | 56 | 39.6 | 1.90 (±0.12) | 41 | 44.3 | 1.48 (±0.12) | 30 | 50.8 | 1.15 (±0.13) |
| SERUM c-erbB-2 | 57 | 39.6 | 1472.15 (±78.78) | 41 | 44.3 | 1515.63 (±155.48) | 30 | 50.8 | 3490.67 (±364.48) |
| SERUM c-erbB-2 (UNITS/mg PROTEIN) | 57 | 39.6 | 28.04 (±0.63) | 41 | 44.3 | 33.05 (±3.44) | 30 | 50.8 | 85.97 (±9.31) |
| SERUM CA 15-3 (UNITS/ml) | 42 | 38.0 | 10.88 (±0.74) | 33 | 43.9 | 15.91 (±0.88) | 30 | 50.8 | 41.49 (±10.65) |
| SERUM PROTEIN (mg/ml) | 56 | 39.3 | 53.04 (±1.41) | 44 | 44.3 | 42.90 (±1.16) | 30 | 50.8 | 42.15 (±1.58) |

FIG. 8

FREQUENCY DISTRIBUTION FOR QUESTIONNAIRE DATA

| CHARACTERISTIC | CONTROLS | BENIGN TUMORS | MALIGNANT TUMORS | p-VALUE |
|---|---|---|---|---|
| n | 57 | 44 | 30 | — |
| TOBACCO USAGE | — | — | — | 2.40E-06 |
| YES | 3 | 15 | 16 | — |
| NO | 54 | 29 | 14 | — |
| RACE | — | — | — | 0.00063 |
| CAUCASIAN | 38 | 13 | 12 | — |
| AFRICAN-AMERICAN | 19 | 31 | 18 | — |
| SYSTEMIC DISEASES | — | — | — | 0.334 |
| YES | 16 | 17 | 10 | — |
| NO | 41 | 23 | 20 | — |
| PRESCRIBED MEDICATIONS | — | — | — | 0.449 |
| YES | 25 | 23 | 16 | — |
| NO | 32 | 18 | 14 | — |
| MENOPAUSAL STATUS | — | — | — | 0.00016 |
| PREMENOPAUSAL | 40 | 19 | 9 | — |
| PERIMENOPAUSAL | 0 | 10 | 17 | — |
| POSTMENOPAUSAL | 17 | 15 | 4 | — |

FIG. 9

MEAN AND STANDARD ERROR OF THE MEAN (S.E.M.) VALUES
VALUES FOR c-erbB-2 AMONG VARYING MALIGNANT TUMOR STAGES

| CHARACTERISTIC | | SALIVA | | SERUM | |
|---|---|---|---|---|---|
| CLINICAL T STAGE | n | c-erbB-2 (UNITS /ml) MEAN (S.E.M.) | c-erbB-2 UNITS / mg PROTEIN MEAN (S.E.M.) | c-erbB-2 UNITS / mg PROTEIN MEAN (S.E.M.) | c-erbB-2 UNITS / mg PROTEIN MEAN (S.E.M.) |
| T1 | 7 | 211.15 (±25.91) | 133.75 (±10.27) | 3428.13 (±564.29) | 95.57 (±16.83) |
| >T1 | 16 | 190.50 (±19.36) | 137.01 (±17.85) | 3680.15 (±605.42) | 89.32 (±14.60) |

MEAN AND STANDARD ERROR OF THE MEAN (S.E.M.) VALUES
VALUES FOR c-erbB-2 AMONG NODE POSITIVE AND NODE NEGATIVE CANCER PATIENTS

| TUMOR SIZES | n | c-erbB-2 (UNITS /ml) MEAN (S.E.M.) | c-erbB-2 UNITS / mg PROTEIN MEAN (S.E.M.) | c-erbB-2 UNITS / ml MEAN (S.E.M.) | c-erbB-2 UNITS / mg PROTEIN MEAN (S.E.M.) |
|---|---|---|---|---|---|
| NODE NEGATIVE | 16 | 192.70 (±21.02) | 119.52 (±12.74) | 2296.36 (±308.42) | 87.44 (±8.83) |
| NODE POSITIVE | 7 | 227.25 (±14.36) | 192.42 (±29.19) | 5308.55 (±2066.35) | 126.63 (±49.54) |

FIG. 10

CUTOFF VALUES, SENSITIVITY, SPECIFICITY, AND PERCENT AREA UNDER CURVE
FOR SALIVARY AND SERUM c-erbB-2 AND CA 15-3 CONCENTRATIONS

| CHARACTERISTICS | CUTOFF VALUE | SENSITIVITY | SPECIFICITY | PERCENT AREA UNDER CURVE |
|---|---|---|---|---|
| SALIVA c-erbB-2 | 110 | 0.87 | 0.65 | 75.7 |
| SALIVA c-erbB-2 (UNITS / mg PROTEIN) | 100 | 0.77 | 0.77 | 76.7 |
| SALIVARY CA 15-3 | 4 | 0.62 | 0.79 | 70.5 |
| SERUM c-erbB-2 | 2000 | 0.94 | 0.60 | 76.7 |
| SERUM c-erbB-2 (UNITS / mg PROTEIN) | 50 | 0.84 | 0.68 | 76.0 |
| SERUM CA 15-3 | 20 | 0.75 | 0.44 | 62.2 |

FIG. 11

METHOD OF DIAGNOSING AND MONITORING MALIGNANT BREAST CARCINOMAS

This application is a Continuation-in-Part of U.S. application Ser. No. 09/259,993 filed Mar. 1, 1999, now U.S. Pat. No. 6,294,349, and claims priority benefit therefrom.

BACKGROUND OF THE INVENTION

This invention relates generally to the use of salivary biomarkers to diagnose breast cancer and, more particularly, to diagnostically differentiate between women with carcinoma of the breast, women with benign tumors, and healthy controls.

Breast cancer is the second leading cause of death among women in the United States. Approximately 1 woman in every 10 will develop breast cancer in her lifetime. Recent statistics estimate that 44,000 women will die of breast cancer, while 150,000 new female cases of breast cancer will be diagnosed in the next year.

It has been shown that screening for breast cancer can reduce breast cancer mortality. Among women aged 50 and older, studies have demonstrated a 20% to 40% reduction in breast cancer mortality for women screened by mammography and clinical breast examination. However, among women between 40 to 49 years of age, the mortality rate is reduced only 13% to 23%. These results suggest that further methods of screening could potentially reduce the mortality in the younger age group of women.

While physical examination and mammography are useful screening procedures for the early detection of breast cancer, they can produce a substantial percentage of false positive and false negative results especially in women with dense parenchymal breast tissue. For example, the probability of having a false negative mammographic examination is 20% to 25% among women between 40 to 49 years of age and 10% among women 50 to 69 years of age. Consequently, screening will result in a number of negative biopsy results yielding a high percentage of false positives. There is also a demonstrated lack of sensitivity in detecting cancerous lesions in younger women yielding a significant percentage of false negatives.

There has also been a clear need for added modalities of screening to help diagnose cancer in younger women. Increased technology in the field of mammography has allowed more reliable detection of small lesions of the breast; while, researchers in the field of breast cancer continue to seek additional adjunct diagnostic procedures to further enhance cancer screening and, thereby, to reduce mortality rates.

During the past three decades, cancer researchers have made extensive use of immunohistochemistry to detect expression of specific biomarkers that may be used as adjunct diagnostic procedures in the diagnosis of certain tumors. (Grizzle WE. Biomarkers-The New Frontier in the Pathology of Invasive and Preinvasive Neoplasias. Biotechnic and Histochemistry, 72(2):59–61, 1997; Grizzle W E, Myers R B, Manne U. The Use of Biomarker Expression to Characterize Neoplastic Processes. Biotechnic and Histochemistry, 72(2):96–104, 1997.) Tumor markers such as c-erbB-2 (erb) and Cathespin-D (CD) have been assayed in tissue and shown to correlate with aggressive lesions. The majority of the investigations performed have used these markers in tissues and serum.

With respect to specific cancer antigens in saliva, Chien found that saliva contained CA 125, a glycoprotein complex that is a recognized or accepted tumor marker for epithelial ovarian cancer. (Chien DX, Schwartz PE, CA 125 Assays for Detecting Malignant Ovarian Tumors. Obstetrics and Gynecology, 75(4):701–704, 1990.) In comparing salivary CA 125 concentrations among healthy controls, women with benign lesions, and those with ovarian cancer, Chien found a significantly elevated CA 125 concentration among the ovarian cancer group as compared to the nonmalignant controls. Boyle detected and identified tumor-specific mutations using radio-labeled oligonucleotide in preoperative salivary samples of individuals suffering from head and neck squamous cell carcinoma. These findings were demonstrative in 71% of the patients studied. (Boyle JO, Mao L, Brennan JA, Koch W M, Eisele D W, Saunders J R, Sidransky D. Gene Mutations in Saliva as Molecular Markers for Head and Neck Squamous Cell Carcinomas. Am J Surgery, 168(5):429–32, 1994.)

SUMMARY OF THE INVENTION

However, such antigens are not diagnostic for breast cancer, and the aforementioned tumor biomarkers (e.g., CA 125, erb and CD) have not been tested for their presence in saliva. While the diagnostic methods of the prior art have generally progressed, such innovations have not been extended to all areas of diagnosis. There is a need for a method to more fully utilize recent technological advances and apply them to the detection and treatment of breast carcinomas.

Accordingly, it is an object of the present invention to use saliva as a diagnostic medium and/or as part of a non-invasive protocol for the detection and differential diagnosis of breast carcinomas, thereby overcoming various deficiencies and shortcomings of the prior art, including those outlined above.

It can be another object of the present invention to identify one or more biomarkers present in saliva, as having diagnostic value and/or as can be used in post-treatment monitoring or therapy. Likewise, it can be another object to provide one or more biomarkers as part of a diagnostic panel for the initial detection, follow-up screening for detection, reoccurrence of breast cancer in women, response to chemotherapy and/or surgical treatment of the disease state.

It can also be an object of the present invention to determine one or more appropriate concentration cut-off values for biomarkers diagnostic for the initial detection, follow-up screening for detection, recurrence of breast cancer in women, chemotherapeutic response and/or surgical treatment of the disease state.

It can be another object of the present invention to provide a method of using serum and salivary cut-off concentrations for diagnostic biomarkers to compare detection rates and/or sensitivities. Likewise, it can also be an object of the present invention to provide a method of using receiver operator curves and related analyses to determine cut-off concentrations for a variety of salivary biomarkers having diagnostic value in the detection and/or treatment of breast carcinomas.

It can also be an object of the present invention to use saliva as a medium to determine nodal status of a patient diagnosed with a breast carcinoma. Likewise, it can be a further object of this invention to identify one or more biomarkers present in saliva in the determination of nodal status.

It can also be an object of the present invention to use saliva to determine the receptor status of a biomarker present therein, as part of a differential diagnosis of breast carcinoma. Likewise, the present invention can also include a method of using receptor status of a biomarker present in saliva as an indication of tumor aggressiveness.

It would be understood by those skilled in the art that one or more aspects of this invention can meet certain objectives, while one or more other aspects can meet certain other objectives. Each objective may not apply equally, in all instances, to every aspect of the present invention. As such, these objectives—in light of the prior art regarding diagnosis of breast cancer—can be viewed in the alternative with respect to any one aspect of the present invention.

Other objects, features, benefits and advantages of the present invention will be apparent from this summary and the following inventive examples, and will be readily apparent to those skilled in the art having knowledge of the nature and detection of cancer biomarkers and their use in the diagnosis of corresponding disease states. Such objects, features, benefits and advantages will be apparent from the above as taken in conjunction with the accompanying examples, tables, data and all reasonable inferences to be drawn therefrom.

In part, the present invention is a method of using a salivary biomarker to differentially diagnose and/or detect reoccurrence of breast carcinoma. The method includes (1) using a human saliva specimen to provide a salivary biomarker for that individual and diagnostic for carcinoma of the breast, (2) comparing the individual biomarker with a biomarker reference, and (3) differentially identifying the diagnosis for the individual as indicated by the biomarker comparison. The biomarker reference can be made up of a panel of constituents and can be developed using malignant tumor, benign tumor and control group populations. Each referenced biomarker constituent can have associated with it a range of values comparable to a corresponding individual biomarker.

In preferred embodiments, the individual biomarker is one constituent of a biomarker panel, and the reference panel includes one or more biomarkers identified as having diagnostic value. Such biomarkers can include cancer antigen 15-3, tumor suppressor oncogene protein 53 and oncogene c-erbB-2. In highly preferred embodiments of the inventive method, the presence of oncogene c-erbB-2 and/or an increased expression of protein identifies an individual as having a malignant carcinoma.

Each individual biomarker constituent can be associated with a concentration value, for comparison with a corresponding reference constituent. In one embodiment of the present invention, the concentration of cancer antigen 15-3 for an individual having a malignant breast tumor is at least about 100 percent higher than such a concentration for an individual having a benign tumor. Likewise, in a preferred methodology, the concentration of oncogene protein 53 for an individual having a malignant breast tumor is at least about 25 percent lower than an individual having a benign tumor. Such differential identifications can be used alone or in conjunction with one or more primary diagnostic methods for the testing and detection of breast carcinomas.

In part, the present invention is a post-operative method of monitoring tumor growth. The method includes (1) providing an individual post-operative to the removal of a malignant tumor, (2) using a saliva specimen from that individual to develop a post-operative biomarker panel, (3) comparing the post-operative biomarker panel with a pre-operative biomarker reference panel for the individual, and (4) determining the presence of malignancy by monitoring at least one constituent of the respective biomarker panels.

Typically, and in preferred embodiments of this method, post-operative chemotherapy is administered to the individual. The chemotherapy can include but is not limited to a therapeutic regimen of cyclophosphamide, methotrexate and fluorouracil. In preferred embodiments, both biomarker panels include a c-erbB-2 constituent, the post-operative detection of which indicates tumor reoccurrence. Alternatively, both biomarker panels can include tumor suppressor oncogene protein 53 as a constituent, the post-operative absence of which indicates rumor inhibition.

In part, the present invention is a method of using the concentration of an endogenously encoded protein to diagnose carcinoma of the breast. The method includes (1) using a saliva specimen from an individual to provide a protein biomarker diagnostic for carcinoma of the breast, (2) comparing the individual protein biomarker with a reference protein, and (3) determining an elevated concentration of the individual protein biomarker over the referenced protein to diagnose the individual. In preferred embodiments, the biomarker protein is one constituent of a biomarker panel. Likewise, the reference protein can be one constituent of a reference panel. Regardless, any such protein can be developed as a reference using malignant tumor, benign tumor and control group populations. In highly preferred embodiments, the individual protein biomarker is cancer antigen 15-3 or, alternatively, an expression of oncogene c-erbB-2.

The biomarkers of the present invention can include any proteinaceous expression, fragment or bioderivative, or ligand or antibody thereto, encoded by any oncogenetic material, which has or can be characterized biochemically, physiologically or structurally.

For instance. CA 15-3 has been characterized as a mucinous glycoprotein and shown to be a diagnostic indicator. More specifically, CA 15-3 is a carcinoma-associated antigen which is identified by two monoclonal antibodies designated Mab D 11-5 and Mab DF3. Mab D 11-5 is prepared against an antigen of human milk fat globule membranes, and Mab DF3 is generated against membrane fraction from human breast cancer.

It has also been observed that the c-erbB-2 oncogene (also referred to as HER-2/neu), which is capable of transforming cells to malignancy, is present in some tumors at very high levels [Zhou et al., *Cancer Research*, 47:6123 (1987); Berger et al., *Cancer Research*, 48:1238 (1988); Kraus et al., *The EMBO Journal*, 6 (3):605 (1987); and Slamon et al., *Science*, 235:177 (1987)]. The expression of the c-erbB-2 oncogene, and its location in the external membrane of cells appears to be closely associated with cancer [Kraus et al., id; Slamon et al. id; Drebin et al., Cell, 41:695 (1985); and Di Fiore et al., *Science*. 237:178 (1987)]; it may, in fact, be the primary event in the development of cancer in at least some cases [Muller et al., *Cell*, 54:105 (1988)]. Overexpression of the c-erbB-2 protein on the surface of normal cells appears to cause them to be transformed or otherwise behave as tumor cells.

Evidence of such transformation can be found, of course, proximate to the disease. Underlying many facets of diagnostic utility, however, is the discovery that c-erbB-2 overexpressing cells shed the c-erbB-2 external domain into neighboring tissues. Derivatives of e-erbB-2 have been found in the serum of stably transformed expressing cells.

A glycoprotein having an approximate molecular weight of 75 kilodaltons (kd) has been identified to constitute the external domain of the approximately 185 kd glycoprotein (gp 185) that is c-erbB-2. The term "gp 75" is precisely defined by its nucleotide and amino acid sequences; the gp 75 external domain comprises the region from about amino acid number 22 (serine; ser-22) to about amino acid number 653 (serine; ser-653) with the nucleotide sequence corresponding thereto. The amino acid sequence represents the nonglycosylated version of gp 75 which would be expected to have a molecular weight corresponding thereto.

The gp 75 proteins and polypeptides are encoded by the gp 75 external domain DNA sequence (nucleotides encoding from approximately ser-22 to approximately ser-653) or by fragments of said gp 75 DNA sequence. The phrase "gp 75 proteins and polypeptides" is therefore interpreted to include proteins and/or polypeptides that have substantially the same amino acid sequences or portions thereof, and/or substantially the same biological activity as the gp 75 proteins and polypeptides.

The present invention shows such proteinaceous materials, once found elsewhere, can also be identified and further characterized in saliva. For example and as discussed elsewhere herein, it was undertaken to determine if the oncogene, HER-2/neu, was present in Stimulated Whole (SWS), Parotid (P2), submandibular/sublingual (S2) and/or Minor (M2) salivary secretions among six healthy, age matched women. Because of its relationship with saliva, gingival crevicular fluid (GCF) was also assessed. HER-2/neu assays were performed by ELISA. HER-2/neu concentrations were assayed in serum and compared to those of saliva. Assays revealed the presence of HER-2/neu in SWS (40.71 Units/ml), PS (15.71 Units/ml), and S2 (14.08 Units/ml) with only trace amounts appearing in M2 and GCF. SWS produced the highest levels of HER-2/neu as compared to glandular secretions. Overall and as might be expected, the greatest concentration of HER-2/neu appeared in serum. However, when HER-2/neu concentrations were corrected for total protein, the higher concentrations appeared in P2 (72.78 Units/ml) secretions, with lesser amounts excreted in SWS (34.01 Units/ml) and S2 (34.95 Units/ml) by comparison.

Such results indicate that the protein, HER-2/neu, is present in saliva and is conveyed, primarily, by the parotid gland. The results also indicate that HER-2/neu may passively diffuse from the serum, to the interstitium, and then be excreted by saliva into the oral cavity. A growing body of work relates to saliva constituents and mechanisms of salivary secretion (See *Glandular Mechanisms of Salivary Secretion*, Edited by Garrett et al., (1999) and the references cited therein), demonstrating skill in the art correlating serum and salivary proteins.

In accordance with the present invention, proteins—in addition to the c-erbB-2 proteins described herein—distinctly associated with either breast cancer or other carcinogenic disease states have been or can be analyzed or characterized in a manner similar to that described above for the c-erbB-2 oncogene. As would be known to those skilled in the art and subsequently made aware of this invention, those other distinctly disease associated proteinaceous expressions, whether identified proximate to the disease or found serially, are detectable in saliva and can be evaluated as described herein for use as salivary biomarkers diagnostic for associated disease states.

The biomarkers and related inventive method can be used for detecting breast carcinoma and provide for an economical and logistical adjunct diagnostic test for mammography. Furthermore, these salivary markers can also, in conjunction with physician and self breast examination, help to reduce morbidity and mortality rates for breast cancer and thereby reduce overall national health care expenditures.

BRIEF DESCRIPTION OF THE DRAWINGS

FIG. 1 is a compilation of mean values for healthy controls, individuals having benign lesions and carcinomas in situ (Ca in Situ), comparing saliva and serum media: ‡=erb control (saliva)<erb cancer group (saliva) one way sample test t-test (mean vs constant): t-value=14.31, $p>0.0001$: ‡‡=erb control (serum)<erb cancer group (serum) one way sample t-test (mean vs constant) t-value=10.33, $p<0.0001$; #=CA 15-3 control & benign (saliva)<CA 15-3 cancer group (saliva) Anova $p<0.05$; and # #= CA 15-3 control & benign (serum)<CA 15-3 cancer group (serum) Anova $p<0.01$.

FIG. 8 presents mean and standard error values determined for various serum and salivary erb characteristics.

FIG. 9 presents questionnaire data obtained from the indicated groups studied, showing the utility of the present invention.

FIG. 10 shows erb values determined by malignant tumor stage.

FIG. 11 shows a series of cut-off values for erb and CA 15-3 concentrations, in accordance with the various diagnostic methods of this invention.

EXAMPLES OF THE INVENTION

Figure 2:
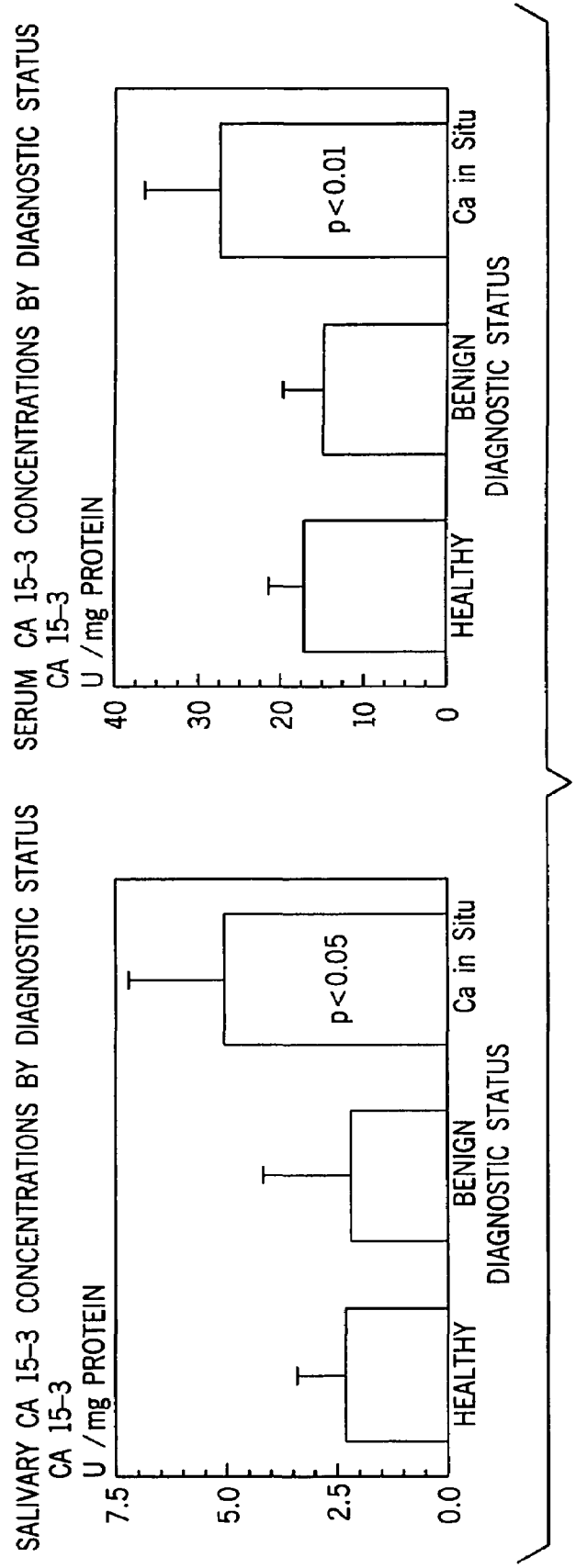
FIG. 2 is a tabular comparison of salivary and serum concentrations (U/mg protein) of CA 15-3, by diagnostic status.

The following non-limiting examples and data illustrate various aspects and features relating to the method(s) of the present invention, including the surprising and unexpected results obtained thereby.

With respect to the following examples and data, the subject population consisted of 21 women from the general population (controls) and the University of Mississippi Medical Center (UMMC), Department of Oncology and Surgery Clinics (tumor patients). Individuals with a breast mass were referred to UMMC from the surrounding community for evaluation. Each patient was given a thorough physical examination and evaluated for carcinoma of the breast. Saliva and serum specimens were collected from each women at the initial visit at the clinic and prior to receiving any treatment. Final pathologic diagnostic evaluations later revealed whether the individual had a benign tumor, or carcinoma of the breast (m situ). Investigators were initially blind with respect to diagnostic outcome of the subjects until a final diagnosis was rendered by the pathologist and the patient referred for further treatment. The subjects were racially mixed and ranged in age from 30 to 80 years.

False positive results were eliminated. It was initially envisioned that the present methodology might provide false positives due to extraneous physiological and environmental factors such as estrogen levels and smoking, respectively. However, such factors have been eliminated as providing false positive results. Race, age, menopausal status, medication usage and health status were also eliminated as factors producing false positive results.

Assays were determined as indicated using the referenced commercial kits and associated reagents, procedures and/or techniques. Kits from Triton Diagnostics are no longer available. Kits from CIS bio international are particularly useful and provide enhanced sensitivity, especially with regard to the erb marker.

Example 1

Statistical Analysis. Statistical analysis were performed using the SPSS statistical software package. A descriptive analysis was made comparing mean marker values for the controls, those with benign tumors, and carcinoma of the breast.

A one-way analysis of variance for unbalanced data, the general linear models procedure, was used to compare the mean values for the group with breast carcinoma with a non cancer groups. The polynomials formulated using the general linear models procedure are easy to interpret and are appropriate for all sample sizes including those too small to sustain an appropriate multivariate analysis. The Tukey post-hoc analysis was used for significant linear models.

Considering that erb was undetected among controls and benign lesions for both saliva and serum, a one way sample t-test was performed. Due to the small sample size, issues concerning the specificity and sensitivity of the panel of markers were not addressed, but will be investigated in subsequent studies.

Example 2

Specimen Collection. Stimulated whole saliva specimens were collected for a 5 minute period using a cube of paraffin as a stimulant (Navasesh, 1982)[17] Salivary flow rates were determined gravimetrically. All specimens were collected in the morning thereby controlling for any possible effects that circadian rhythm may produce in marker concentration. Samples can be frozen for future analysis. Blood was also drawn at the time of saliva collection by a phlebotormist. None of the participants exhibited cancerous or precancerous lesions in the oral cavity at the time the specimens were collected.

The frozen saliva samples were thawed and centrifuged at 500–1500 G for 20 min to precipitate cells and mucin in order to extract the bio-marker proteins. The clear saliva extract and the serum from the blood specimens were analyzed for total protein and the panel of biomarkers.

Example 3

Total Protein. A colorimetric assay for measuring total protein concentration, based on the color change of Coomassie brilliant blue G-250 dye in response to various concentrations of proteins, was used (Bio-Rad Kit). Specimens were read on a spectrophotometer and absorbance measured at 595 nm. Total protein concentration of the samples was determined from a standard curve constructed with bovine gamma globulin standards.

Example 4

CA 15-3. CA 15-3 assays were determined by using EIA kits (CIS bio international). The CA 15-3 assay is a two-site solid phase enzyme immunoassay. The molecules of CA 15-3 are "sandwiched" between two monoclonal antibodies, the first one attached to the ELSA solid phase and the second one linked to the horseradish peroxidase (enzymatic conjugate). After washing, the enzymatic reaction develops a color proportional to the amount of CA 15-3 present in the assay. Absorbances are read at 490 nm using a spectrophotometer and concentrations are calculated from standard curves constructed from known concentrations of the ligand. The CA 15-3 assay is designed to assay serum specimens. Saliva supernatants were substituted in place of the serum for salivary CA 15-3 determinations. The antibodies used in the test do not present cross-reaction with other known tumor markers (CEA, CA 19-9, CA 125) and the salivary concentrations are substantially above the lower limit of detection for the assay. CA 15-3 concentrations were expressed as units/mg of protein.

Example 5 erb and pantropic p53. erb and pantropic p53 assays were determined using ELISA kits (Oncogene Research, Co.). In this study serum and the salivary supernatant were substituted m place of the tissue extracts as assay specimens. A colormetric evaluation of the level of binding was performed and the intensity of the color formed by the enzymatic reaction is proportional to the target protein present. Absorbances were read at 490 nm in a microplate spectrophotometer and ligand concentrations calculated from standard curves, erb and p53 data were expressed as units/mg of protein and pmol/mg of protein, respectively. The antibodies used in the test do not present cross-reaction with other known tumor markers and the salivary concentrations are substantially above the lower limit of detection for the assay.

Example 6

Cathepsin-D Assay. Salivary and serum CD concentrations were determined using enzyme immunoassay (ELA) kit (T ton Diagnostics. Inc.). A monoclonal antibody and a rabbit polyclonal antibody both specific for CD were simultaneously incubated with both the saliva and serum specimens. During the incubation, the CD present in the saliva and serum specimens was bound by the two anti-CD antibodies. The monoclonal antibody is conjugated to biotin causing the formed antigen-antibody complex to be bound onto the streptavidin-coated tube. Unbound materials were removed by washing the tubes. In the second incubation, an anti-rabbit antibody conjugated with horseradish peroxidase was added to the tube. The conjugate was then bound to the complex. Unbound complex was removed by a second washing. The tubes were then incubated with a TMB substrate solution in order to develop a color. Phosphoric acid was then added to stop the enzymatic reaction. The intensity of the color that was developed was determined using a spectrophotometer set at 450 nm. Specimen values were determined from the curve which resulted by plotting the absorbance values of the controls against the known concentrations (pmol/mg of protein).

Example 7

Epidermal Growth Factor Receptor. EGFR assays were determined using EIA kits (Triton Diagnostics. Inc.). The anti-EGFR conjugate was incubated with the saliva and serum specimens. During the incubation the EGFR protein becomes bound by the anti-EGFR conjugate. One of the monoclonal antibodies is conjugated to horse radish peroxidase. During the second incubation the resulting immune complexes become bound onto a coated polystyrene tube by a "linking solution". Unbound substrates were then washed by decanting. The tubes were then incubated with a TMB substrate solution in order to develop a color. Phosphoric acid was then added to stop the enzymatic reaction. The intensity of the color that was developed was determined using a spectrophotometer set at 450 nm. Specimen values were determined from the curve which resulted by plotting the absorbance values of the controls against the known concentrations (fmol/mg of protein).

For all their power, immunoassays are subject to many kinds of interference. The investigators performed several test laboratory tests to control for these problems. With respect to ligand recovery, the investigators were able to establish the amount of marker (ligand) recovered from saliva and serum samples. Five saliva and serum specimens with known amounts of marker were serially diluted. The dilutions were assayed for all three markers. The data were plotted against the expected values to determine the linearity of dilution. The slopes of both the dose response curve and the standard curve were not significantly different from each other and the intercepts were not significantly different from zero. During the assaying of the specimens, the investigators employed the use of appropriate positive and negative controls for all marker assays. When performing the assays, some test specimens contained primary antibodies preincubated with excess ligand to control for false positives. In addition, test specimens were preincubated with excess free primary antibody to determine if the signal had been eliminated. These extra tests provided additional quality control during the course of specimen analyses. When assayed, all specimens were run in triplicate.

The control group consisted of 15 women (age 42.4), the benign tumor group consisted of 8 women (age 45.3), and the cancer group consisted of 12 women (age 49.0). The subjects diagnosed with benign lesions consisted of women with fibroadenomas (n=4), lipomas (n=1), and fibromas (n=3). The women with breast cancer were diagnosed with lobular carcinoma (n=1), infiltrating ductal carcinoma (n=9), and ductal carcinoma in situ (n=2). All of the subjects with carcinoma of the breast were node negative and without evidence of metastases. Five of the cancer subjects among the cancer group were edentulous while only two among the non-cancer group were edentulous. All other subjects were dentate. The mean values for the three groups are shown in FIG. 1 and illustrated graphically in FIGS. 2-7.

As shown in FIGS. 1 and 2, the mean values for CA 15-3 among the controls and benign lesions group were approximately 45%–50% lower than the mean value for the cancer group. This was statistically significant at the $p<0.05$ level for saliva and $p<0.01$ level for serum.

Figure 3:
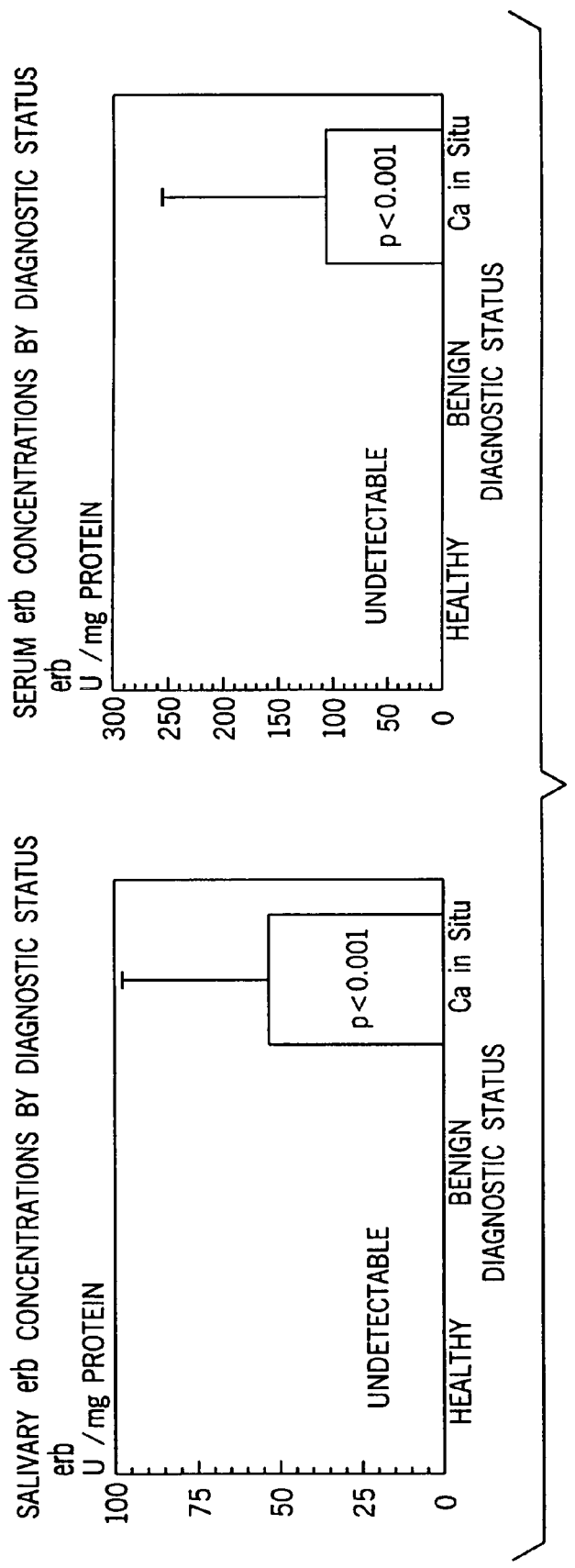
FIG. 3 is a tabular comparison of salivary and serum concentrations (U/mg protein) of erb, by diagnostic status.
Figure 4:
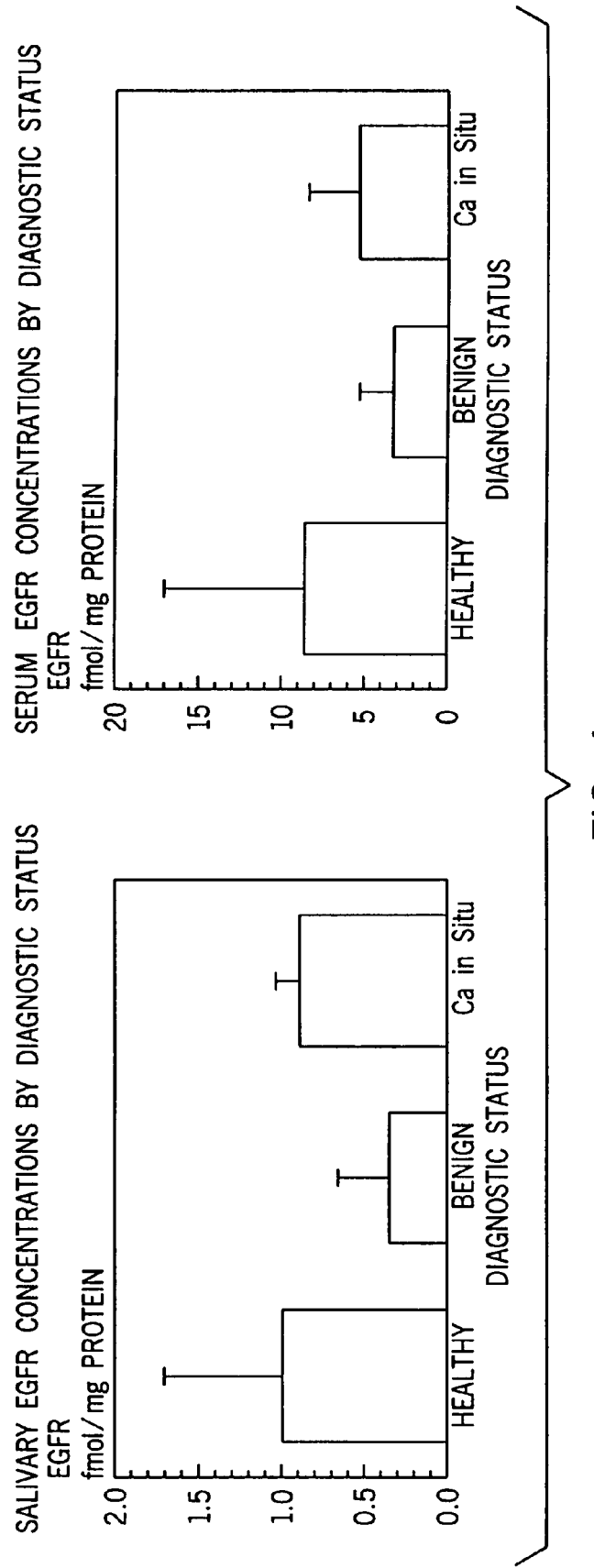
FIG. 4 is a tabular comparison of salivary and serum concentrations (fmol/mg protein) of EGFR, by diagnostic status.
Figure 5:
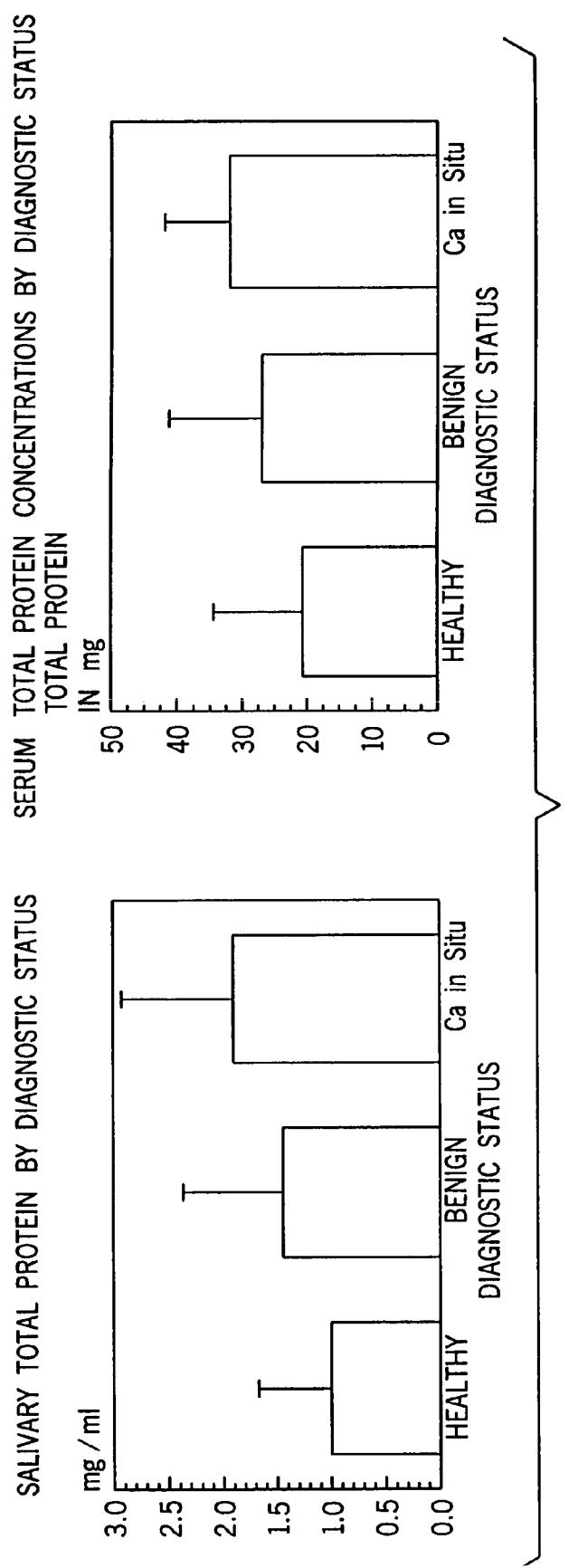
FIG. 5 is a tabular comparison of salivary and serum total protein concentrations (mg/ml), by diagnostic status.

Referring to FIGS. 1 and 3, erb was not detected in the saliva or the serum of the controls or benign lesions group. Conversely, the carcinoma group exhibited the presence of erb and the t-test showed significantly higher concentrations ($p<0.001$).

Figure 6:
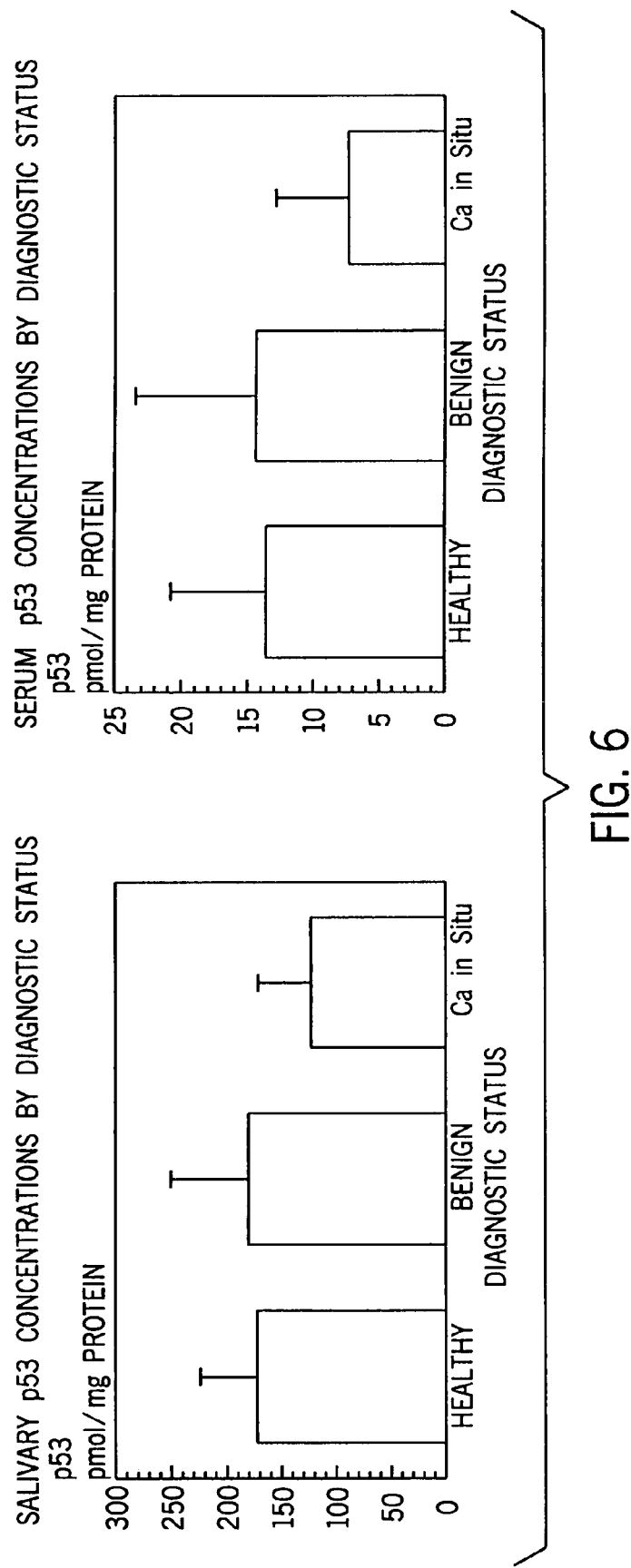
FIG. 6 is a tabular comparison of salivary and serum concentrations (pmol/mg protein) of p53, by diagnostic status.
Figure 7:
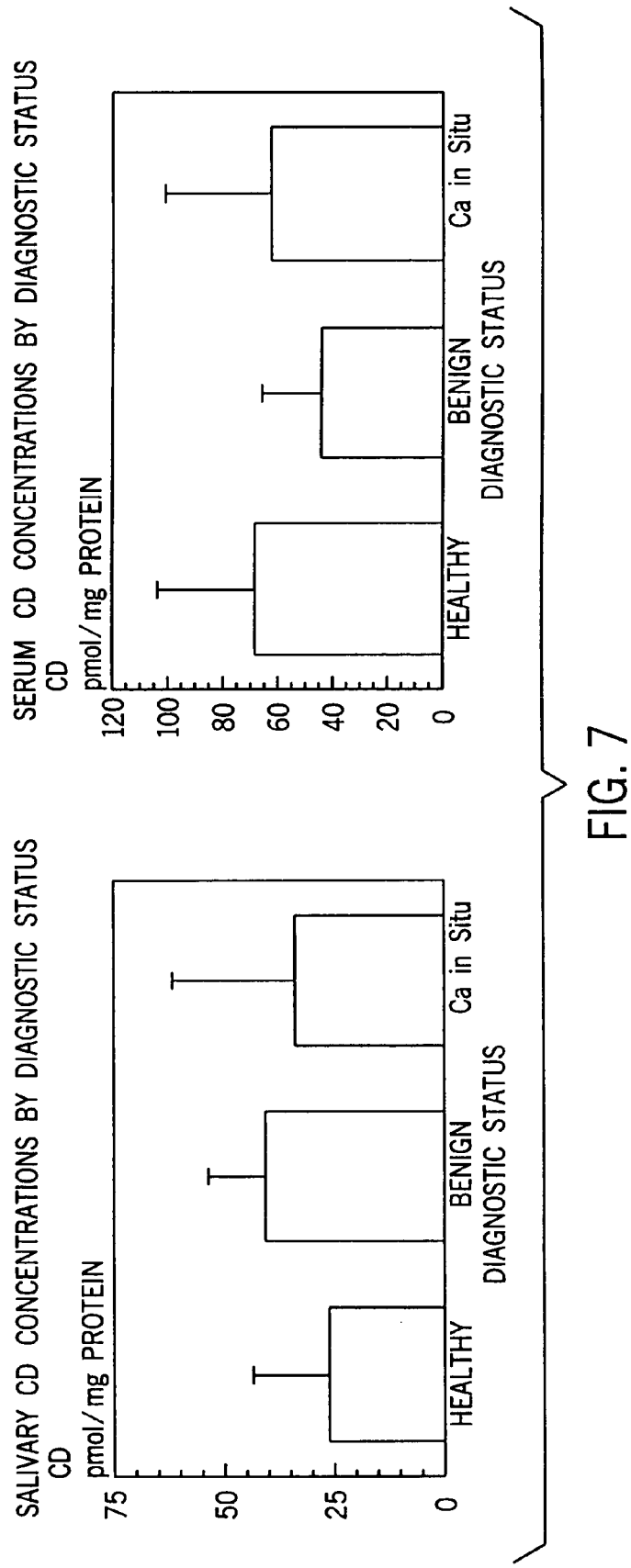
FIG. 7 is a tabular comparison of salivary and serum concentrations (pmol/mg protein) of CD, by diagnostic status.

Additionally, p53 levels were approximately 25% higher among the controls and the benign lesion groups as compared to the cancer group (FIGS. 1 and 6.) The investigators expected higher p53 values among the controls as compared to those women with breast cancer in so far as p53 mutation reflects the inability of the oncogene to render tumor suppression. As shown in the accompanying figures, saliva and serum levels of CD and EGFR did not appear to be as tumor specific as CA 153, erb and p53 when compared across the three groups of women.

Example 8a

With respect to the presence of the panel of markers in saliva, several technical issues were also addressed. One such issue was to determine if cells from the oral epithelium may possibly contribute to marker levels found in the saliva. To address this, salivary specimens were centrifuged and the supernatant separated from the pellet. A sample from the supernatant was placed on a glass slide, stained and microscopically examined for the presence of cells. The examination disclosed the absence of cells in the supernatant. Next, the pellet was resuspended in phosphate buffered saline. Both the supernatant and the resuspended pellet were analyzed for the presence of the biomarkers. The results showed biomarker levels in the supernatant, but an absence of biomarkers in the resuspended pellet, indicating the biomarkers originate in the saliva and that there are no biomarker contributions from the cells.

Example 8b

A second experiment was performed using secretory IgA (sIgA) as a control protein to compare individuals with and without carcinoma of the breast. The predominant immunoglobulin in saliva is sIgA. It is derived from salivary glands with the parotid gland being the principal producing gland. The antibody is synthesized as IgA dimers by immunocytes present in the major and minor salivary glands. Because of its ability to attenuate pathogenic assault, sIgA is consider to be the oral cavity's first line of defense. This salivary protein has no relationship with carcinoma of the breast and was selected as a control protein. Using ELISA methodology, sIgAs were detected in the saliva from both the cancer and the non-cancer groups. The results of this test showed no significant differences among those individuals with ($\bar{x}$11.7 ng/ml) and without cancer ($\bar{x}$14.3 ng/ml), indicating that the only proteins which appear to be elevated are those markers associated with carcinoma of the breast.

Example 8c

A third experiment was performed to determine the effects of oral health on the marker levels. A small number of individuals with periodontal disease was compared to healthy controls and several edentulous subjects. The results showed no significant difference in marker levels among those with periodontal disease, those who were orally healthy and those who were edentulous.

Example 8d

A fourth experiment was conducted to determine the effects of the estrous cycle on salivary marker levels. Two healthy women with regular menses had saliva specimens collected daily from the beginning of their menstrual cycle to its end. The results showed no major fluctuations of salivary marker concentrations occurring during the menstrual cycle. Marker concentrations were relatively consistent over the 30 day period suggesting minimal individual variability (data not shown).

Example 8e

Another experiment was conducted to determine the origin of the salivary gland constituents. Parotid, submandibular, sublingual and minor gland secretions were collected. The results of this experiment indicate that these markers are primarily secreted by the parotid gland. Parotid gland secretions were found to be many times higher than the submandibular, and sublingual concentrations. Minor gland contributions were barely detectable. Additionally, marker concentrations appear to be flow rate independent.

As shown above, detectable levels of the breast tumor markers CA 15-3, erb, EGFR, CD, and p53 were present in the saliva and serum of women with malignant breast lesions. These markers are also detectable in the saliva and serum of women with benign breast lesions and completely healthy individuals. The results also indicate lower levels of CA 15-3, erb, in noncancer individuals as compared to those with breast carcinoma (FIG. 1). The reverse was true with respect to p53.

Several potential confounding factors were also considered and resolved. Accordingly, it was determined that: the cells from the oral epithelium did not contribute to the marker levels, 2) using sIgA as a control protein, the only proteins which are elevated are those markers associated with carcinoma of the breast, 3) the presence of periodontal disease has no effect on marker levels, 4) the estrous cycle had no effect on salivary marker levels, 5) the markers are secreted primarily from the parotid gland and 6) are flow rate independent.

A similar study consisted of three groups of women: Group I was a control group. This group consisted of healthy, asymptomatic individuals from the University of Mississippi Medical Center (UMMC). Health status for the control group was determined by questionnaire.

Group II, the benign tumor group, and Group III, the malignant tumor group, consisted of consecutive individuals from the surrounding community with a breast mass that were referred by a physician to UMMC Division of Oncology for evaluation. Each patient received a thorough physical examination and was evaluated for carcinoma of the breast. Saliva and serum specimens were collected from each women at the initial clinic appointment and prior to receiving any treatment. Final diagnostic evaluations obtained from pathology reports determined whether the individual would be classified to Group II, the benign tumor group, or to Group III, the group diagnosed with carcinoma of the breast. Staging and nodal status were assessed according to the criteria set forth by the American Joint Committee on Cancer.

All participants were administered a brief questionnaire at the time of signing the IRB approved consent form. This data was collected by interview and included information concerning their age, race, tobacco usage, pharmacological and medical histories, and menopausal status.

Similar to the procedures and/or examples discussed above, stimulated whole saliva specimens were collected for a 5 minute period using a cube of gum base as a stimulant following standardized collection procedures. Upon collection, the specimens were aliquoted and frozen for analysis. Salivary flow rates were determined gravimetrically. All specimens were collected in the morning thereby controlling for any possible effects that circadian rhythm may produce in marker concentration. Blood was also drawn at the time of saliva collection by a phlebotomist.

The frozen specimens were thawed and the saliva and the serum from the blood specimens were analyzed for total protein and the c-erbB-2 concentrations.

The specimens were also assayed for CA 15-3. The effectiveness of CA 15-3 as a diagnostic marker is documented in the literature and was used as a reference marker or "diagnostic gold standard" by which to compare the efficacy of the c-erbB-2 marker.

Samples of saliva were assayed for protein using the bicinchoninic acid method (Pierce Chemical. Co.) which is a highly sensitive and selective detection reagent for the cuprous ion. This method measures protein concentrations from 0.5–20 mg/ml. In this assay, bicinchoninic acid serves as a chelating agent for $Cu^{-1}$ forming a color complex in the presence of protein. Aliquots of saliva (100 $\mu$L) were placed in microtiter plates and the Pierce BCS protein assay reagent added to the wells. Samples were incubated for 30 minutes at 37° C. and the optical density read at 562 nm in a microplate spectrophotometer. The final concentration of each substance was derived from a standard curve and data was expressed as mg/mL.

Serum and salivary extracellular domain c-erbB-2 antigen levels were assayed using ELISA kits from Oncogene Research Products. Whole saliva was substituted in place of serum as assay specimens. The basic assay involves a colormetric evaluation of the level of binding which was performed and the intensity of the color formed by the enzymatic reaction being proportional to the target protein present. The absorbance was read at 490 nm in a microplate spectrophotometer and the ligand concentration calculated from a standard curve. c-erbB-2 data were expressed and reported as both Units/ml and Units/mg of protein so that these findings could be compared to previous results in the literature.

CA 15-3 assays were determined by using EIA kits from CIS Bio International. The CA 15-3 assay is a two-site solid phase enzyme immunoassay. The molecules of CA 15-3 are "sandwiched" between two monoclonal antibodies. The first one is attached to the ELISA solid phase and the second one linked to the horseradish peroxidase (enzymatic conjugate). After washing, the enzymatic reaction develops a color proportional to the amount of CA 15-3 present in the assay. Absorbance is read at 490 nm (horseradish peroxidase) using a spectrophotometer and the concentration is calculated from a standard curve constructed from known concentrations of the ligand. The CA 15-3 assay is designed to assay serum specimens. Whole saliva was substituted in place of the serum for salivary CA 15-3 determinations. CA 15-3 concentrations were expressed as Units/ml.

Statistical analyses were again performed using the SPSS™ statistical software package. These data were analyzed from four different perspectives. Initially, the saliva and serum marker concentrations were summarized for each group and descriptive analyses were conducted for the demographic and supplemental data obtained from the questionnaire. The focus was on race, medical status, tobacco use, medication usage, and menopausal status with respect to c-erbB-2 concentrations. The data were summarized by tumor type, staging, and nodal status. Due to the small number of women in the cancer group, the number of sub-categories for primary tumor (T) and nodal status (N) were collapsed. The primary tumor categories were dichotomized to T1 and greater than T1, while nodai status was reduced to node negative and node positive, respectively.

A one-way analysis of variance (ANOVA) was used to compare the mean marker values for the three groups, focusing on the breast cancer in contrast to the non-cancer groups. The Dunnett's test was used to adjust for multiple comparisons.

Possible associations among the salivary and serum c-erbB-2 levels as well as those between c-erbB-2 and CA 15-3 concentrations in saliva and serum were investigated by Pearson's correlation coefficient. As the distribution of some of these concentrations were skewed, the data were transformed using the square root of each value.

Example 9

Receiver operating characteristic (ROC) analyses were conducted to investigate the appropriate cut-off values for each biomarker. Separately for each marker their concentrations were recoded into dichotomous variables using the mean of the control and the cancer group as the initial cut-off value. Incremental ranges of cut-off values in a positive ($>\bar{x}$) and negative ($<\bar{x}$) direction about the mean were assessed for each marker. Breast cancer was dichotormized into positive and negative. Two-by-two tables were used to compute the sensitivity and specificity values of each biomarker for detecting disease for each cut-off value. ROC curves (sensitivity vs 1-specificity) were constructed for c-erbB-2 and CA 15-3 concentrations in both saliva and serum. The optimum cut-off value for each marker was determined by using the cut-off value that produced the largest percentage of area under its ROC curve. See. Wilcosky TC. Chapter 3, Criteria for selecting and evaluating markers. In: Hulka BS. Wilcosky TC. Griffith JD, eds: *Biological Markers in Epidemiology*, New York. Oxford University Press, 1990, pp. 36–42: and SPSS for Windows, release 9.0. Chicago: SPSS, 1999.

Example 10

Demographic and supplemental data obtained from the questionnaire were conducted for the three groups of women are summarized in FIGS. 8 and 9. Frequency comparisons by race, tobacco use, medication use and menopausal status were conducted. There were significant differences in race, tobacco use, and menopausal status among the three groups. More African-Americans experienced carcinoma of the breast and benign tumor lesions than Caucasians. Likewise, significantly more tobacco users experienced carcinoma of the breast and benign tumor lesions than non-users. With respect to menopausal status, perimenopausal women experienced carcinoma of the breast and benign tumor lesions than the pre and postmenopausal women. Mean c-erbB-2 values were compared for each group according to health status (e.g. control, benign, cancer). There were no significant reportable effects on c-erbB-2 concentration attributable to these variables within each group of women (health status). Age comparisons yielded no significant group differences for c-erbB-2 values and was not linearly related to c-erbB-2 values when regression modeling was employed.

Further analyses showed that the women with breast cancer produced detectable salivary levels of c-erbB-2 that were significantly higher than those produced by the benign tumor and the control groups. The means, standard error of the means, and the 95% confidence intervals for the salivary marker concentrations across the three groups are shown in FIGS. 8, 12–14. As shown in FIG. 8, the mean c-erbB-2 values for the control and benign tumor groups were approximately 50%–57% lower than the mean value for the cancer group. A strong parallel response in the corresponding serum c-erbB-2 levels was evidenced in these women, with an associated range of 55% to 64%, although the concentrations in serum were roughly 15 times higher than those in saliva before correcting for total protein.

The majority of the benign tumors were fibroadenoma or fibrocystic tumors. There was little difference between salivary c-erbB-2 concentrations found in fibroadenoma and fibrocystic tumors among women who had these benign tumors. Two women presented with fluid filled cysts and two with benign calcifications. Both the serum and saliva c-erbB-2 values for the fluid filled cysts were statistically lower than those for the fibroadenoma and fibrocystic groups. Again the responses in serum were similar to those in saliva for these two groups of benign tumors, although the rank ordering of the observed average concentrations reversed between the fibroadenoma and fibrocystic groups.

The vast majority of tumors in the cancer group were infiltrating ductal carcinomas (n=19). One woman had an infiltrating lobular carcinoma, three had a ductal carcinoma, and seven had miscellaneous breast malignancies. The mean salivary and serum c-erbB-2 concentrations for these groups were all substantially higher than those observed for the benign tumors.

With respect to the staging of the cancer tumors, there was one Stage 0 (T0N0M0) patient, six were Stage I (T1N0M0), eight Stage ILA (T2N0M0), three Stage IIB. The IIB group was composed of one T2N1M0 and two T3N0M0. There were two Stage IIIA composed of one T3N0M0 and one T3N2M0, three Stage IIIB composed of one T3N3M0 and two T4N1M0. Seven patients were not staged at the time the data of this example was made available.

Seven subjects with carcinoma of the breast were node positive and 16 were node negative. All individuals diagnosed with cancer were without evidence of distant metastases. The sub-categories for primary tumor were collapsed into T1 and greater than T1 and node positive and node negative groups (FIG. 10). These analyses showed no differences with respect to tumor size for c-erbB-2 saliva and serum concentrations, but there was an elevated c-erbB-2 concentration difference between node positive and node negative individuals regardless of diagnostic medium (FIG. 10).

Example 11

The second level of analyses compared group means for the women with carcinoma of the breast, women with benign lesions, and the healthy control group. A one-way ANOVA for unbalanced data was performed across the three categories of women for salivary c-erbB-2 and was found to be significant at the F=13.83; p<0.0001 level. The Dunnett's C post-hoc analysis exhibited a significant difference between the cancer group and the benign tumor and control groups at the p<0.001 level.

A similar result was demonstrated for serum c-erbB-2 across the three groups of women. The overall ANOVA was significant at the F=19.95; p<0.0001 level with the post-hoc analyses significant at the p<0.001 level (cancer >both non-cancer groups).

With respect to CA 15-3, the overall ANOVA was significant at the F=5.94; p<0.04 level with the post-hoc analyses significant at the p<0.05 level (cancer >non-healthy control group). Similarly, the results for serum c-erbB-2 across the three groups of women were significant at the F=20.96; p<0.0001 level with the post-hoc analyses significant at the p<0.001 level (cancer >healthy control group).

Data for the salivary and serum c-erbB-2 levels corrected for total protein concentrations exhibited the same results as the non-corrected data. The overall ANOVA for salivary c-erbB-2 was significant at the F=13.80; p<0.0001 level with the post-hoc analyses significant at the p<0.001 level (cancer >both non-cancer groups). The results for serum c-erbB-2 across the three groups of women were significant at the F=14.45; p<0.0001 level with the post-hoc analyses significant at the p<0.001 level (cancer >both non-cancer groups).

Example 12

The third level of analyses, correlations coefficients, revealed a significant moderate association between serum and salivary c-erbB-2 at the r=0.51; p<0.0001 level. There was a significant, moderate association between serum c-erbB-2 and serum CA 15-3 concentrations at the r=0.40: p<0.001 level. With respect to serum c-erbB-2 concentrations corrected by total protein and their association with CA 15-3, the results exhibited a significant, moderate association r=0.36; p<0.001 level. A slight relationship was found between salivary c-erbB-2 concentrations corrected by total protein and serum c-erbB-2 concentrations corrected by total protein at the r=0.39; p<0.001 level.

Example 13

Figure 12A:
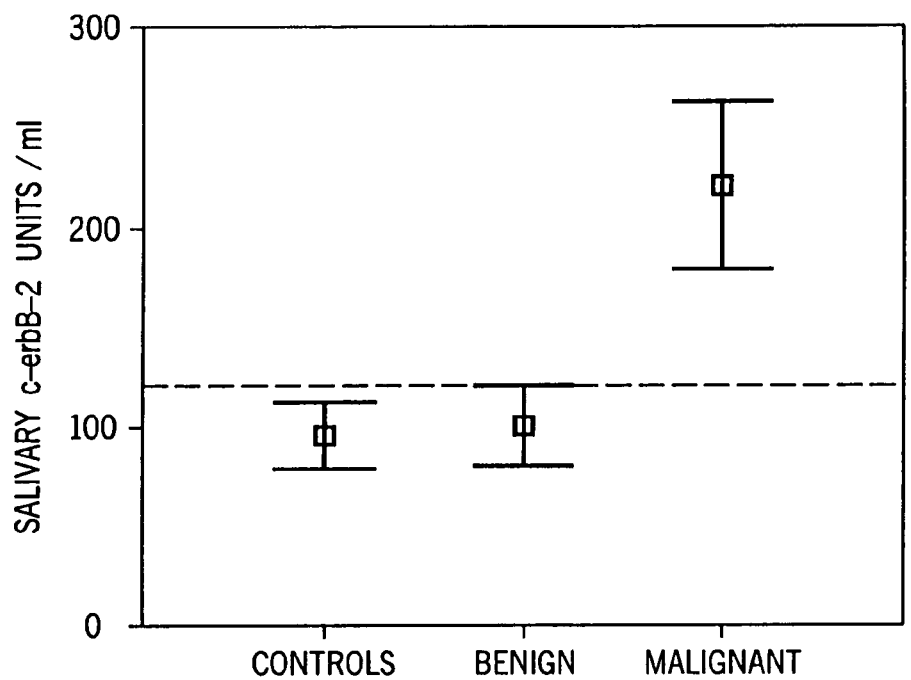
FIG. 12a shows graphically mean values, 95% Confidence Intervals, and cut-off value (110 Units/ml) for salivary c-erbB-2 Units/ml for the control group, group diagnosed with benign lesions, and the group diagnosed with carcinoma of the breast.
Figure 12B:
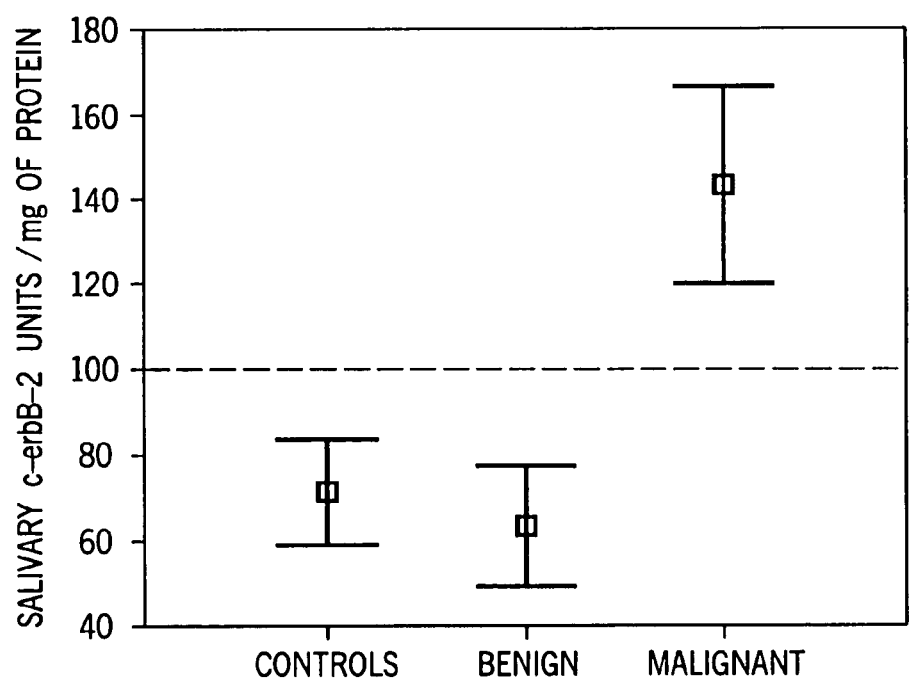
FIG. 12b shows graphically, mean values, 95% Confidence Intervals, and cut-off value (110 Units/ml) for salivary c-erbB-2 Units/mg of protein for the control group, group diagnosed with benign lesions, and the group diagnosed with carcinoma of the breast.
Figure 13A:
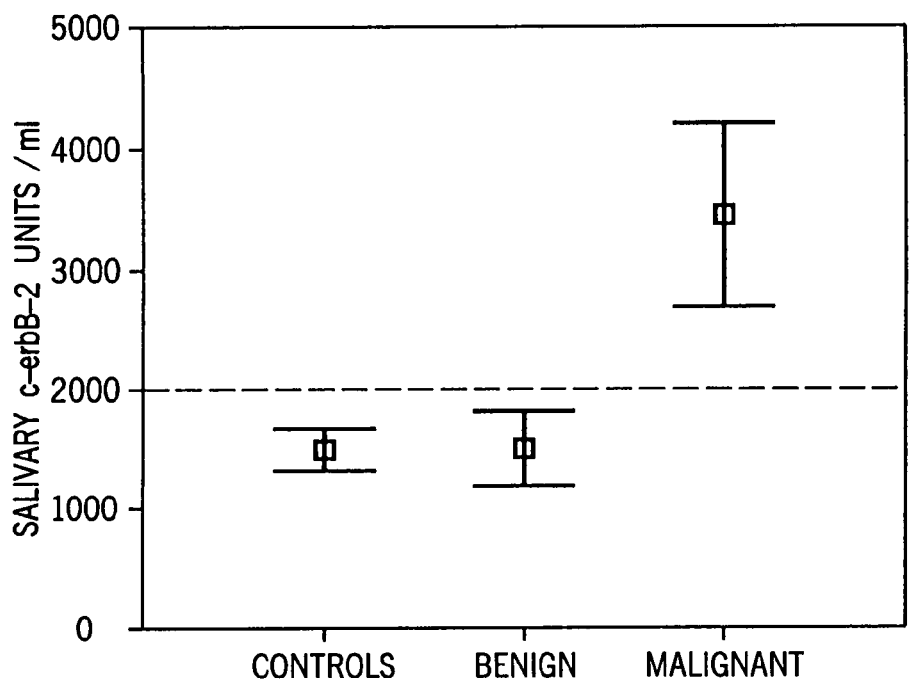
FIG. 13a shows, a graphically, mean values, 95% Confidence Intervals, and cut-off value (2000 Units/ml) for serum c-erbB-2 Units/ml for the control group, group diagnosed with benign lesions, and the group diagnosed with carcinoma of the breast.
Figure 13B:
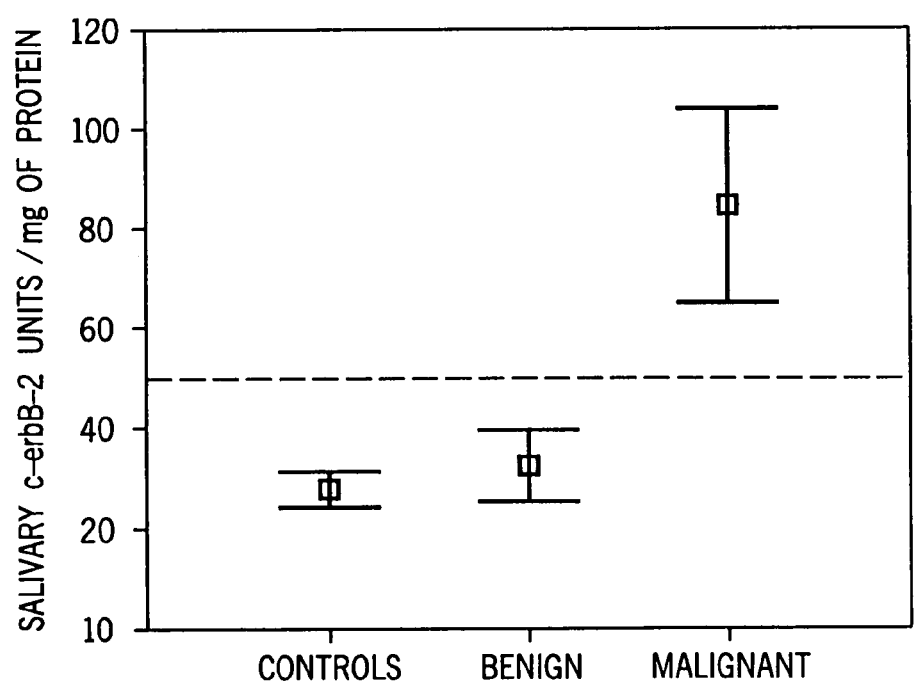
FIG. 13b shows graphically mean values, 95% Confidence Intervals, and cut-off value (50 Units/ml) for serum c-erbB-2 Units/mg of protein for the control group, group diagnosed with benign lesions, and the group diagnosed with carcinoma of the breast.
Figure 14A:
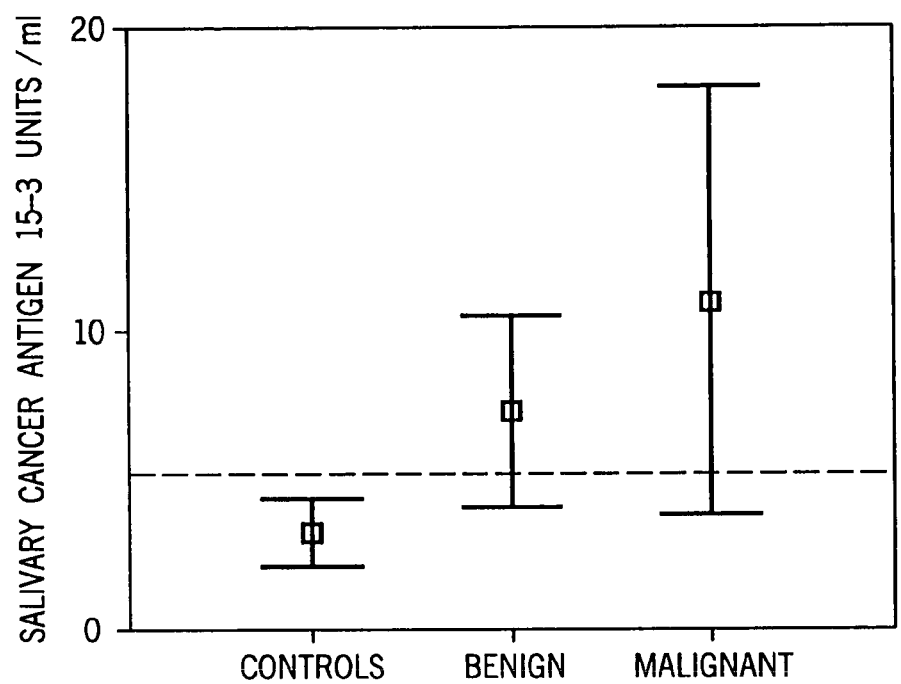
FIG. 14a shows graphically mean values, 95% Confidence Intervals, and cut-off value (4.0 Units/ml) for salivary CA 15-3 Units/ml for the control group, group diagnosed with benign lesions, and the group diagnosed with carcinoma of the breast.
Figure 14B:
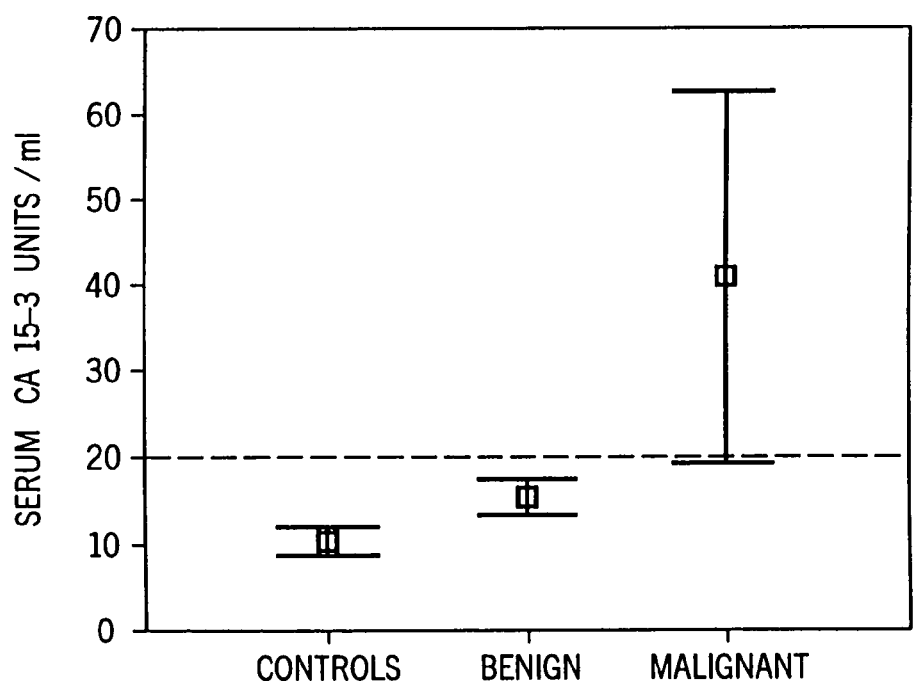
FIG. 14b shows graphically mean values, 95% Confidence Intervals, and cut-off value (20 Units/ml) for serum CA 15-3 Units/ml for the control group, group diagnosed with benign lesions, and the group diagnosed with carcinoma of the breast.

The comparison of receiver operator curves (fourth level analyses) suggested a cut-off value of 110 Units/ml for salivary and 2000 Units/ml for serum c-erbB-2 concentrations (FIGS. 11, 12a and 13a). A comparison of receiver operating characteristic curves was also performed on salivary and serum c-erbB-2 concentrations corrected by total protein. These values were 100 Units/ml and 50 Units/ml for salivary and serum c-erbB-2 concentrations (FIGS. 11 and 12b and 13b). Salivary CA 15-3 determinations yielded a 4.0 Units/ml cut-off value (FIGS. 11 and 14a). The cut-off value for serum CA 15-3 was 20 Units/ml (FIGS. 11 and 14b), compared to literature values ranging from 15–40 Units/ml.

Figure 15:
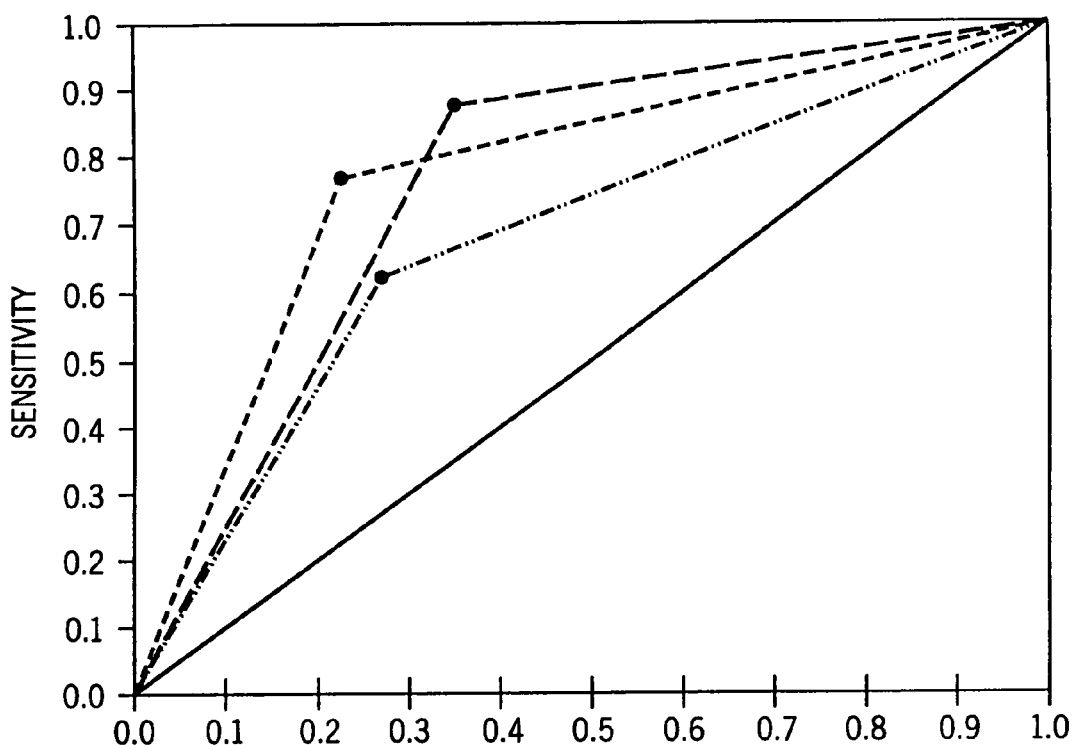
FIG. 15 shows a graphic plot of receiver operating characteristic (ROC) curves (sensitivity vs. 1-sensitivity) for salivary c-erbB-2 Units/ml (- -), salivary c-erbB-2 Units/mg of protein (••••), and salivary CA 15-3 Units/ml (-••-); the percent area under each curve is as follows: c-erbB-2~76%, a cut-off of about 110 units/ml: c-erbB-2/tp~77%, a cut-off of about 100 Units/mg protein; and CA 15~3~71%, a cut-off of about 4 Units/ml.
Figure 16:
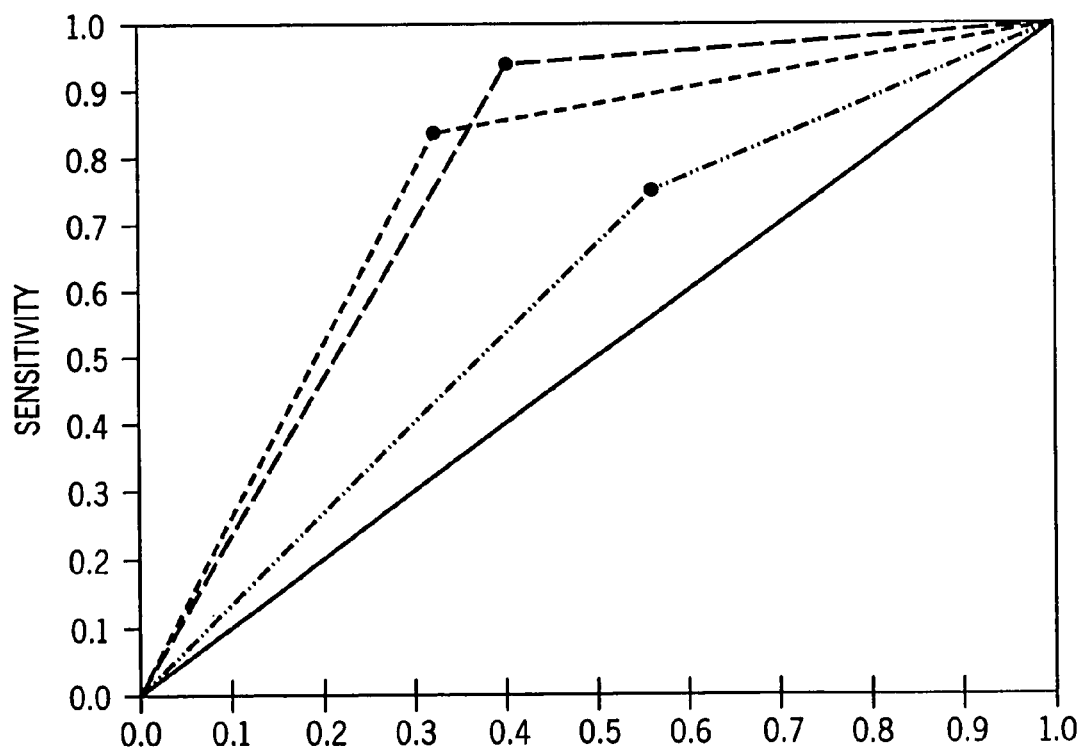
FIG. 16 shows graphically receiver operating characteristic (ROC) curves sensitivity vs 1-sensitivity) for serum c-erbB-2 Units/ml (- -), serum c-erbB-2 Units/mg of protein (•••••), and serum CA 15-3 Units/ml (-••-); percent area under each curve is as follows: c-erbB-2~77%, a cut-off of about 2000 Units/ml; c-erbB-2/tp~76%, a cut-off of about 50 Units/mg protein; and CA 15-3~71%, a cut-off of about 20 Units/ml.

Using the aforementioned cut-off values, salivary and serum c-erbB-2 concentrations were able to detect 87% and 94% of the subjects with cancer, respectively (FIG. 11). The salivary and serum c-erbB-2 concentrations corrected by total protein detected 77% and 84% of the subjects. This compares to 62% and 75% for the salivary and serum CA 15-3 marker. CA 15-3 levels were able to detect 65% of the malignant lesions (FIGS. 11, 15 and 16).

Example 14

Prior studies involving the c-erbB-2 oncoprotein vary in the types of populations studied with respect to staging, tumor type, nodal involvement, and the presence of metastases. Additionally, a variety of analytical techniques have been used to study the c-erbB-2 oncoprotein in both tissue and serum. With respect to serum, most studies have used enzyme-based immunoassays. These techniques have varied with respect to the sensitivity of the assays and the use of either monoclonal or polyclonal antibodies. Some kits used in the literature have since been discontinued and are no longer available to researchers. The findings herein are compared with studies using similar, sample sizes, staging, and assay technology.

The results of the preceding examples suggest elevated salivary c-erbB-2 and serum c-erbB-2 levels among women with carcinoma of the breast (FIGS. 8 and 12-14). With respect to elevated serum c-erbB-2 levels among breast cancer patients, the findings of this study agree with others found in the literature particularly those evaluating non-metastatic cancer. There is only one report on the literature concerning elevated salivary c-erbB-2 concentrations among women with breast cancer and that was a preliminary study performed by the authors of this investigation. This earlier study used EIA (Triton, Co.) assay for determining salivary and serum c-erbB-2 concentrations. The results of that study also revealed significantly higher salivary c-erbB-2 concentrations among women with carcinoma of the breast. The assay employed in this study, when compared to the assay of the first study using the same identical specimens, appears to be five times more sensitive than the original assay.

Example 15

Benign and malignant tumor comparisons yielded potentially useful information. Subjects with fibroadenomas and fibrocystic lesions produced similar salivary and serum c-erbB-2 concentrations (FIG. 9). For serum, this finding compares with results obtained by Breuer (1998). Subjects diagnosed with infiltrating ductal carcinoma dominated the cancer population in this study. Consequently, comparisons among the various types of malignant breast lesions were not made.

Example 16

Further analyses of the primary tumor data revealed no substantial salivary or serum c-erbB-2 concentration differences for groups T1 and greater than T1 (FIG. 10). This observation does agree with the findings of Watanabe (1994) and Kynast (1993). The finding also suggests that c-erbB-2 receptor status may be more indicative of tumor aggressiveness than tumor volume.

Example 17

With respect to nodal status, node positive patients c-erbB-2 levels were found to be elevated when compared to the node negative subjects (FIG. 9).

Example 18

The data shows an association (r=0.51: p>0.0001) between soluble salivary concentrations of c-erbB-2 and serum levels of c-erbB-2. The unexplained variability may be attributed to the "pooling" of the various types of individuals across the three groups of women and the fact the investigators do not discern the exact mechanism by which the c-erbB-2 protein migrates from the tumor site and enters the oral cavity (diffusion, leakage, active transport). The process by which c-erbB-2 protein becomes solubized is also not fully understood and may account for a portion of the unexplained variability. Further investigation, currently underway, is exploring this line of inquiry. The association between salivary and serum c-erbB-2 concentrations that were corrected by total protein concentrations was r=0.39: p<0.001.

Example 19

A relationship between serum c-erbB-2 concentrations and serum CA 15-3 levels was found (r=0.40, p>0.001). This correlation was in agreement with the results reported by Krainer (r=0.396; p>0.002). When the serum c-erbB-2 concentrations were corrected by total protein concentrations, the association between serum c-erbB-2 concentrations and serum CA 15-3 levels was r=0.36, D>0.001.

Additionally, the data of previous examples also suggest that salivary c-erbB-2 and serum c-erbB-2 levels may be equivalent to salivary CA 15-3 and serum CA 15-3 levels as diagnostic markers (FIGS. 11, 15 and 16). The salivary and serum c-erbB-2 concentrations were able to detect 87% and 94% of the subjects with cancer, respectively. The salivary and serum c-erbB-2 concentrations corrected by total protein detected 77% and 84%, respectively, of the subjects. This compares to 62% and 75% for the salivary and serum CA 15-3 marker. CA 15-3 levels were able to detect 75% of the malignant lesions at a 20 Units/ml cut-off value. The manufacturer recommended a 15 Units/ml cut-off value and indeed the sensitivity did increase to 97%; however, when this adjustment was made a sharp decline in specificity (35%) resulted as predicted by Stenman (1991). Conversely, when the cut-off value was increased to 40 Units/ml, the ability of the assay to detect cancer decreased to less than 30%. This is in agreement with the findings of Safi (1991) and Stenman (1991). Serum c-erbB-2 levels, whether corrected for total protein or not, retained a margin of specificity at the 60% level for sensitivities over 90%.

Example 20

Information from the health questionnaire concerning age, race, tobacco usage, presence of systemic disorders, use of prescription medications, and menopausal status was also analyzed. These analyses confirmed the results from prior reports published by the investigators that these variables have no effect on salivary and serum c-erbB-2 concentrations. Additionally, the findings for age (Watanabe, 1994), tobacco usage (Breuer, 1998), and menopausal status (Breuer, 1998) are supported by other studies; however, our study disagrees with Breuer (1998) which observed age related influences on marker concentrations. Breuer (1998) reported that among postmenopausal women, age was significantly related to c-erbB-2 levels.

As a diagnostic medium, saliva has several biochemical advantages. Saliva is a clear, colorless liquid while serum may become milky when lipemic, red when blood cells are hemolyzed due trauma and icteric in the presence of liver disease. These color fluctuations in normal and disease altered serum can affect calorimetric assays such as ELISA, make it difficult to produce a consistent blank and interfere with the true values of the serum assay when compared to the consistent clarity of the assay standards. Since serum possesses more proteins than saliva assaying trace amounts of other factors (i.e., oncogenes, etc.), may result in a greater risk of non-specific interference and a greater chance for hydrostatic (and other) interactions between the factors and the abundant serum proteins.

From a logistical perspective, the collection of saliva is safe (i.e. no needle punctures), non-invasive and relatively simple, and may be collected repeatedly without discomfort to the patient.

The diagnostic benefits arising from the present invention could include the overall management of breast cancer in women. The diagnosis of breast cancer at an earlier stage allows a woman more choice in selection of various treatment options. A saliva based test would be useful in the postoperative management of cancer patients. Following tumor removal, an expected decrease in marker concentration should follow and eventually plateau to within a normal level indicating that the patient is free of disease. In contrast, a persistently high level of salivary markers may be indicative of tumor recurrence or persistence. Saliva could also be a cost effective method for monitoring the effectiveness of chemotherapy. Individuals should experience decreases in marker concentrations if the treatment regimen is effective.

While the principals of this invention have been described in connection with specific embodiments, it should be understood clearly that these descriptions, along with the chosen tables and data therein, are made only by way of example and are not intended to limit the scope of this invention, in any manner. For example, and without limitation, the methodology described herein can be extended to the diagnosis and monitoring of gall bladder, colon, rectal, pancreatic and oral cancers. Other advantages and features of this invention will become apparent from the following claims, with the scope thereof determined by a reasonable equivalents, as understood by those skilled in the art.

What is claimed is:

1. A method of using a salivary biomarker to differentially diagnose carcinoma of the breast in a human test subject, said method comprising:

providing a salivary secretion specimen from a human subject to provide an individual salivary biomarker diagnostic for carcinoma of the breast, said biomarker soluble in said salivary secretion and selected from the group consisting of cancer antigen 15-3, tumor suppressor oncogene protein 53, oncogene c-erbB-2 and combinations thereof;

using the salivary secretion concentration of said individual biomarker to compare with a protein biomarker reference panel, said reference panel including at least one of cancer antigen 15-3, tumor suppressor oncogene protein 53, oncogene c-erbB-2 protein biomarker, and combinations thereof; and differentially identifying the diagnosis for said subject indicated by said comparison.

2. The method of claim 1 wherein said biomarker reference comprises a constituent panel developed using malignant tumor, benign tumor and control group populations.

3. The method of claim 1 wherein said reference biomarker constituent panel includes concentration ranges for each said constituent.

4. The method of claim 1 wherein the presence of oncogene c-erbB-2 protein biomarker identifies the said subject having a malignant breast carcinoma.

5. The method of claim 1 wherein each said individual biomarker in the reference panel is associated with a concentration value.

6. The method of claim 1 wherein said concentration of cancer antigen 15-3 is at least about 100% higher for a subject having a malignant breast tumor than said subject having a benign tumor.

7. The method of claim 1 wherein said concentration of oncogene protein 53 is at least about 25% lower for a subject having a malignant breast tumor than said subject having a benign tumor.

8. The method of claim 1 wherein said differential identification is an adjunct to a primary diagnostic method of testing said subject for carcinoma of the breast.

9. A post-operative method of monitoring the inhibition of breast tumor growth, said method comprising:

providing a human test subject, said subject post-operative to the removal of a malignant breast tumor;

providing a salivary secretion specimen from said subject to develop a post-operative protein biomarker panel, said panel having constituents selected from the group consisting of cancer antigen 15-3, tumor suppressor oncogene protein 53, oncogene c-erbB-2 protein biomarker and combinations thereof;

comparing said post-operative biomarker panel to compare with a pre-operative biomarker reference panel for said subject; and determining the post-operative inhibition of breast tumor growth by monitoring at least one constituent of said biomarker panels.

10. The method of claim 9 further including administering a chemotherapeutic regimen to said subject post-operatively.

11. The method of claim 10 wherein one said chemotherapy includes a therapeutic dose of cyclophosphamide, methotrexate and fluorouracil.

12. The method of claim 9 wherein said pre-operative and said post-operative panels include a c-erbB2 protein biomarker constituent.

13. The method of claim 9 wherein said pre-operative and said post-operative panels include a tumor suppressor oncogene protein 53 biomarker constituent.

* * * * *